(12) United States Patent
Barnes

(10) Patent No.: US 11,631,501 B2
(45) Date of Patent: Apr. 18, 2023

(54) BODY COMPOSITION PREDICTION TOOLS

(71) Applicant: SELECT RESEARCH LIMITED, Malvern (GB)

(72) Inventor: Richard Barnes, Worcester (GB)

(73) Assignee: Select Research Limited, Malvern (GB)

( * ) Notice: Subject to any disclaimer, the term of this patent is extended or adjusted under 35 U.S.C. 154(b) by 0 days.

(21) Appl. No.: 17/380,771

(22) Filed: Jul. 20, 2021

(65) Prior Publication Data

US 2021/0358633 A1 Nov. 18, 2021

Related U.S. Application Data

(63) Continuation of application No. 16/608,642, filed as application No. PCT/GB2018/051122 on Apr. 27, 2018.

(Continued)

(30) Foreign Application Priority Data

Apr. 28, 2017 (GB) ..................... 1706857

(51) Int. Cl.
*G06T 7/00* (2017.01)
*G16H 50/30* (2018.01)
*G16H 30/40* (2018.01)

(52) U.S. Cl.
CPC .......... *G16H 50/30* (2018.01); *G06T 7/0012* (2013.01); *G16H 30/40* (2018.01); *G06T 2207/10088* (2013.01)

(58) Field of Classification Search
CPC ...... G16H 50/30; G16H 30/40; G06T 7/0012; G06T 2207/10088
See application file for complete search history.

(56) References Cited

U.S. PATENT DOCUMENTS

2013/0315474 A1* 11/2013 D'Amato ............... H04N 19/86
382/154
2016/0287199 A1 10/2016 Watanabe
(Continued)

OTHER PUBLICATIONS

Anonymous: "Waist-hip ratio Wikipedia", Feb. 5, 2017 (Feb. 5, 2017), XP055483677, Retrieved from the internet: URL: https://en.wikipedia.org/w/index.php?title=Waist-hip_ratio&oldid=763914104 [retrieved on Jun. 13, 2018].
(Continued)

*Primary Examiner* — Reginald R Reyes
(74) *Attorney, Agent, or Firm* — Patterson Thuente IP

(57) ABSTRACT

A system for calculating one or more health indicators, comprising a body volume calculator arranged to use measurement data to calculate the volume of at least a part of a subject's body and a length measurement of at least a part of a subject; and processing circuitry arranged to receive information, which may be demographic information, about the subject and the body part volume and length measurements; and to perform at least one of: calculating a predicted Visceral Fat value and/or a predicted Total Body Fat value from the demographic information, the body part volume and length measurements using first and second formulae, which may be empirical formulae, respectively; and calculating a Body Volume Indicator (BVI) arranged to provide an indication of health risk, in particular obesity and cardio-metabolic risk, which may be by using a third formula, which again may be an empirical formula.

16 Claims, 6 Drawing Sheets

Related U.S. Application Data

(60) Provisional application No. 62/491,764, filed on Apr. 28, 2017.

(56) References Cited

U.S. PATENT DOCUMENTS

| | | | |
|---|---|---|---|
| 2017/0124727 A1* | 5/2017 | Amat Roldan | G01B 11/24 |
| 2018/0049695 A1 | 2/2018 | Hector, Jr. | |
| 2018/0268726 A1* | 9/2018 | Kaleal, III | G16H 40/63 |
| 2019/0345251 A1* | 11/2019 | Garito | C07K 16/2863 |

OTHER PUBLICATIONS

Giachetti et al: "Robust Automatic Measurement of 3D Scanned Models for Human Body Fat Estimation", IEEE Journal of Biomedical and Health Informatics, IEEE,Piscataway, NJ, USA, vol. 19, No. 2, Mar. 28, 2014 (Mar. 28, 2014), pp. 660-667, XP011574266.

Heuberger et al: "Body scanning as a new anthropometric measurement tool for health-risk assessment", International Journal of Consumer Studies, Sep. 24, 2007 (Sep. 24, 2207), pp. 35-40, XP055484036, ISSN: 1470-6423.

Goel et al: Predictive Equations for Body Fat and Abdominal Fat with DXA and MRI as Reference in Asian Indians:, Obesity Research, vol. 16, No. 2, Sep. 6, 2012 (Sep. 6, 2012), pp. 451-456, XP055484328, US.

Stan Forth et al: "Generalized abdominal visceral fat prediction medels for black and white adults aged 17-65y: the HERITAGT Family Study", International Journa of Obesity, vol. 28, No. 7, May 18, 2004 (May 18, 2004), pp. 925-932, XP055484289, GB.

Lee et al: "Predictive Equations for Central Obesity via Anthropometries, Stereovision Imaging and MRI in Audits", Obesity Research, vol. 22, No. 3, Dec. 2, 2013 (Dec. 2, 2013), pp. 852-862, XP055484208, US.

Anonymous: "Body fat percentage—Wikipedia", Mar. 29, 2017 (Mar. 29, 2017), XP055484219, Retrieved from the Intrnet: URL: https://en.wikipedia.org/w/index.php?title-=Body_fat_percentage &oldid=772758289 {retrieved on Jun. 14, 2018].

Anonymous: "Viszeralfett—Wikipedica"; retrieved from the internet: https://de.wikipedia.org/w/index.php?title=Viszeralfett&oldid= 161877557.

\* cited by examiner

BODY COMPOSITION PREDICTION TOOLS

CROSS-REFERENCE TO RELATED APPLICATIONS

This application is a continuation of U.S. application Ser. No. 16/608,642 filed Oct. 25, 2019, which is the U.S. national stage filing of PCT Application No. PCT/GB2018/051122 filed Apr. 27, 2018, which claims priority benefits of GB Application No. 1706857.8 filed Apr. 28, 2017 and U.S. Provisional Application No. 62/491,764 filed Apr. 28, 2017, the technical disclosures of which are hereby incorporated herein by reference.

The invention relates to health risk prediction tools for use in health management, and in particular to a biomarker calculated using one or more 3D body part volumes and/or length measurements of a subject, which may be generated from a three-dimensional model of a person, howsoever created. More specifically, the invention relates to methods of calculating and using such a biomarker and to the prediction of "internal" (body composition) data from "external" data including one or more 3D body part volumes and/or lengths. In particular, the biomarker is or comprises a Body Volume Indicator (BVI®), which is calculated using one or more body part volume and/or length measurements of the subject, and demographic information.

Indications of a person's health in the management of healthcare can be configured and represented in different ways; for example as a number, as a series of numbers, as a combination of letters and numbers, or in some cases as one or more symbols.

However, the relevance of that number or designated reference is normally restricted to the medical condition or the type of risk that might be associated with that condition. These numbers or references then become associated with and attributed both to the problem (i.e. the condition that is being treated) and then subsequently used as a barometer or indicator of risk (to provide a healthcare professional with guidelines or project or surrogate risk (i.e. expected outcome as opposed to actual outcome of risk) relevant to the condition). This is more commonly referred to as a barometer of risk or more colloquially as a 'biomarker'. As an example of "surrogate risk", a surrogate risk for cardiovascular disease is a designation that predicts likelihood of someone having a heart attack. The actual outcome is whether or not that person ever does have a heart attack. A surrogate marker of risk is anticipated risk as a result of healthcare factors.

In terms of the biomarkers which are currently used, with reference ranges, in the measurement of the human body, the Body Mass Index (BMI) is currently the most common biomarker of risk for general human health.

First published in 1835 by Adolphe Quetelet, BMI relies on height and weight only to provide an indication of risk referenced against a scale and this is now widely considered to be of value in population statistics only and not suitable for individual risk (for example due to the inability to distinguish between muscle mass and fat mass and different body types). BMI does not distinguish between subjects who have different weight distributions and so have different risk profiles.

This application relates to a particular method suitable for use with the invention described in granted European Patent EP1993443 (Health Indicator) and the granted U.S. Pat. No. 8,374,671 (Health Indicator), which mention that an indication of a person's health can be given as a figure labelled BVI® ("Body Volume Indicator"), which may be calculated using the ratios between the various body part volumes discussed therein.

The present invention builds upon the use of part-volumes of the body in 3D as described in the previous patent.

In summary, the body volume system has undergone a confidential validation and research program involving some of the world's most prestigious and renowned scientific establishments. The invention disclosed herein concerns exemplary processes and procedures, and summarises the data which have been consolidated to produce an inventive biomarker of health risk; comparable in effect and scope to the Body Mass Index. The Body Volume Indicator (BVI®) is intended to become and be recognised as a novel biomarker of risk, offering a unique usage of part volume, and therefore part body shape, to the scientific and healthcare community.

According to a first aspect of the invention, there is provided a system arranged to calculate one or more health indicators, comprising:
 a body volume calculator arranged to use measurement data to calculate the volume of at least a part of a subject's body and a length measurement of at least a part of a subject's body;
 processing circuitry arranged to:
  (i) receive information, which may be demographic information, about the subject and the body part volume and length measurements;
  and to perform at least one of:
  (ii) calculating a predicted Visceral Fat value and/or a predicted Total Body Fat value from the demographic information, the body part volume and length measurements using first and/or second formulae, which may be empirical formulae, respectively; and
  (iii) calculating a Body Volume Indicator (BVI®) arranged to provide an indication of health risk, in particular obesity and cardio-metabolic risk, which may be by using a third formula, which again may be an empirical formula.

The processing circuitry may be provided by a processing unit, for example an Intel® X86 processor such as an 15, 17 processor or the like. The skilled person will appreciate that any suitable processor or the likes known in the art may be used.

Optionally, the BVI® is a single number, which may have one or more digits, optionally including one or more decimal places.

Optionally, one or more body surface area measurements may also be used, for example when assessing risks relative to burn area for burns patients.

According to a second aspect of the invention, there is provided a method of calculating a Body Volume Indicator (BVI®), comprising inputting at least one item of demographic information, at least one body part volume measurement and at least one body length measurement of a subject into an empirical formula for BVI®, the empirical formula being determined from a database comprising corresponding demographic information, body part volume and length information and internal body composition data for a plurality of individuals. Optionally, different databases, or different sections within a database, may be used for different demographic groups of individuals.

Optionally, the internal body composition data are obtained using MRI scans. Optionally, the MRI scans have been processed to obtain Total Body Fat and Visceral Fat data, those data being provided as at least part of the internal body composition data.

Optionally, the internal body composition data and part volumes for the database may be obtained using empirical cadaver data and MRI scans.

Optionally, the at least one item of demographic information for the BVI® formula comprises at least one of age, ethnicity and gender.

Optionally, the at least one body part volume measurement for the BVI® formula comprises abdominal volume.

Optionally, the at least one body length measurement for the BVI® formula comprises at least one of height and waist girth.

Optionally, one or more body surface area measurements may also be used, for example when assessing risks relative to burn area for burns patients.

According to a third aspect of the invention, there is provided a method of calculating a predicted Total Body Fat or Visceral Fat value, comprising inputting at least one item of demographic information, and at least one body length measurement of a subject into an empirical formula for Total Body Fat or Visceral Fat (respectively), the empirical formula being determined from a database comprising corresponding demographic information, body part volume and length information and internal body composition data for a plurality of individuals.

Optionally, at least one body part volume measurement is also input.

Optionally, the at least one item of demographic information for the Total Body Fat or Visceral Fat formula comprises at least one of age, ethnicity, and gender.

Optionally, the at least one body length measurement for the Total Body Fat or Visceral Fat formula comprises at least one of height, hip girth and waist girth. Optionally, age and/or gender may also be included.

Optionally, weight is input.

Optionally, a measure of activity level is input.

According to a fourth aspect of the invention, there is provided a diagnostic tool comprising a Body Volume Indicator determined according to the second aspect of the invention.

Optionally, the diagnostic tool further comprises a predicted Visceral Fat value calculated from external measurements and demographic information.

Optionally, the diagnostic tool further comprises a predicted Total Body Fat value calculated from external measurements and demographic information.

According to a fifth aspect of the invention, there is provided a machine readable medium containing instructions which, when read by a machine, causes that machine to perform the method of the second aspect of the invention.

According to a sixth aspect of the invention, there is provided an indication of health and fitness comprising:
  3D photonic and MRI data;
  a single digit or double-digit whole number;
  a decimal place after the single-digit or double-digit number;
  a series of ranges against which the single-digit number or double-digit number is referenced;
  volumetric measurements of the human body;
  linear measurements of the human body;
  body composition measurements of the human body;
  social information about a human being or beings;
  demographic information about a human being or beings;
  physical attributes about a human being or beings;
  fitness and activity information about a human being or beings;
  dietary information about a human being or beings;
  medical information about a human being or beings;
  reference information about a human being or beings;
  BVI® designation about a human being or beings;
  body database comprising all of the above wherein
    said single-digit number or double-digit number is configured to provide an indication of the health risk or fitness of a person
    said single-digit number or double-digit number is configured to provide an indication of the scale of the health risk or fitness of a person, by reference to a series of ranges
    said single digit number or double-digit number is configured to provide an indication of the health or fitness of said person by retrieving data from the said body database and using a ratio of the said body database information of a new person, then calculating a said indication of health risk to the said database of known persons.

Optionally the single and double digit numbers are arranged to provide the indication of health risk by reference to a designated series of ranges between one single-digit and another single-digit number, between a single-digit and a double-digit number or between a double-digit number and another double-digit number Optionally the volumetric measurements include but are not limited to the volume of the pelvis, abdomen, chest, right arm, left arm, right leg, left leg and neck.

Optionally the linear measurements include but are not limited to waist, hip, chest, thigh girth, neck girth, bicep girth and leg length.

Optionally, the body composition measurements include but are not limited to body fat, visceral fat, muscle, adipose tissue, liver fat, fat free mass, subcutaneous fat and bone.

Optionally, the social information include but are not limited to home location, marital status, employment, background and lifestyle.

Optionally the demographic information include but are not limited to age, gender, ethnicity and socio-economic grouping.

Optionally the physical attributes are to include but are not limited to physical height and weight.

Optionally the fitness and activity information include but are not limited to number of steps taken, frequency of exercise, level of physical activity and attitudes to fitness and activity.

Optionally the dietary information include but are not limited to type of food eaten, volume of food eaten, time of day eaten, types of diets undertaken and attitudes to food.

Optionally the medical information include but are not limited to previous medical history, medical conditions recorded, blood test results and genetic pre-conditions and risk elements.

Optionally the reference information includes but is not limited to a Patient ID number, a Client ID Number, an NHS Reference Number (or equivalent for other health service providers or registers) and a Unique Identifying number, letter or other designation used as a reference.

Optionally the body database includes some or all of the information and measurements described above. The data may be stored and trends tracked for subject and population purposes.

Optionally the BVI® designation includes but is not limited to one or all of the information and measurements described above.

Optionally the indication includes, but is not limited to, a number below or above the number 13.0.

Optionally the ranges include but are not limited to the ranges 0-4.9, 5.0-9.9, 10.0-14.9, and 15.0-20.0.

Optionally the health risk includes but is not limited to Diabetes, High Blood Pressure, Liver Disease, Cancer, Obesity and Improved Health and/or Fitness.

Optionally, comparison information with average or aggregated data of people with similar measurements may be shown.

Optionally, a comparison between any previous indication of a person's health and a present indication of that person's health may be shown.

According to a seventh aspect of the invention, there is provided an indication of health and fitness comprising;
- a body database comprising at least some, and in some cases all, of the information and measurements described with respect to the sixth aspect,
- said single-digit number or double-digit number is configured to obtain an indication of the health risk or fitness of a person;
- said single-digit number or double-digit number is configured to calculate an indication of the scale of the health risk or fitness of a person, by reference to a series of ranges;
- said single digit number or double-digit number is configured to provide an indication of the health or fitness of said person by retrieving data from the said body database and using a ratio of the said body database information of a new person, then calculating a said indication of health risk to the said database of known persons.

Optionally, the body database is used to collect aggregated data statistics, which may be stored in a separate database.

According to an eighth aspect of the invention, there is provided a machine readable medium containing instructions which when read by a machine causes that machine to perform as the indication of health and fitness of the fourth aspect.

According to a ninth aspect of the invention, there is provided a machine readable medium containing instructions which when read by a machine causes that machine to perform as the indication of health and fitness of the fifth aspect.

The skilled person would understand that features described with respect to one aspect of the invention may be applied, *mutatis mutandis*, to the other aspect of the invention.

Reference to a machine readable medium herein, may refer to a transitory or non-transitory media, and will include, but not be limited to any of the following: a floppy disc, a DVD, a CD ROM or RAM, a memory (such as a Flash drive, an SD card, a solid state memory, etc.), a hard drive, a coding process deployed and used on a cloud server, a download (such and Internet download, FTP transfer or the like), a wire, or the like.

The skilled person will appreciate that many features described above in relation to any of the aspects could be provided by software, firmware or hardware and moreover the skilled person will understand the equivalence of the software, firmware and hardware.

There now follows by way of example only a detailed description of embodiments of the present invention with reference to the accompanying drawings in which.

The embodiments described herein relate to a health indicator that can be used in the assessment of a person's (e.g. a patient's) health. The indicator disclosed can also be used as a weight management tool as described below.

It is believed that the health indicator will be used by medical professionals, Dieticians and Nutritionists to monitor weight loss or weight gain in patients, but it may also be used personally. The health indicator may even be used by slimming clubs or for assessment of health insurance premiums, as an alternative to simply being weighed and the person's BMI being calculated manually using just height and weight.

Figure 1:
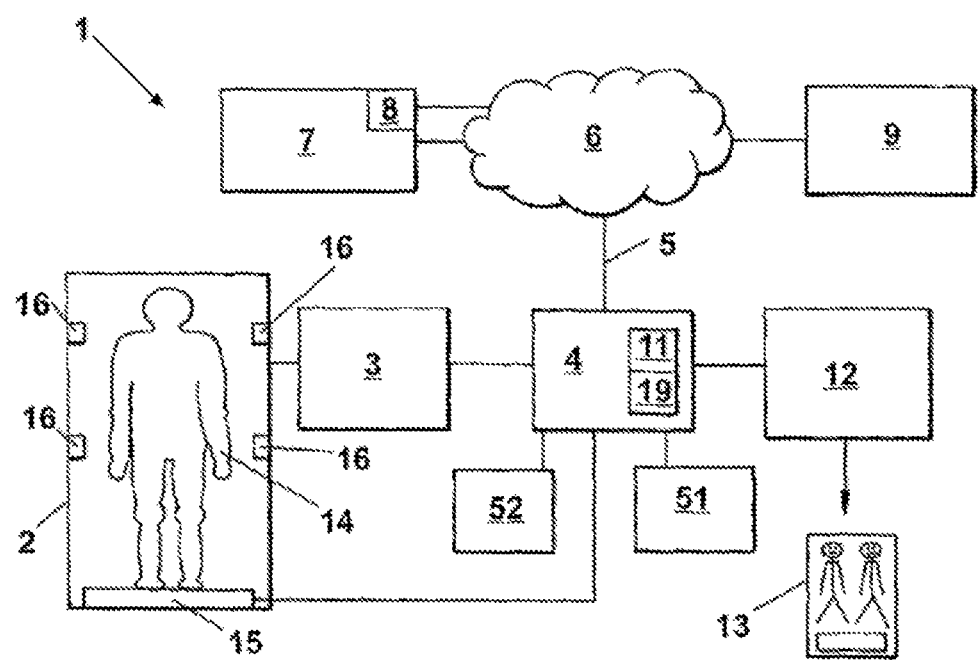
FIG. 1 shows a diagrammatic representation of a health indicator device suitable for calculating BVI® and optionally for use in determining an appropriate formula for the calculation of BVI®.

In FIG. 1, a device 1 suitable for calculating the health indicator (a "health indicator device") is shown comprising a body scanner 2, data collection means 3 and manipulation means 4. In the embodiment being described, the manipulation means 4 has a connection 5 to the Internet 6 so that it can communicate with database means 7. It will be appreciated that the connection need not be via the Internet 6 and may be over a Local Area Network, a direct connection or over a telephone line depending upon the location of the manipulation means 4 and the database means 7. The database means 7 also has access means 8 to enable it to be accessed remotely by healthcare professionals 9 such as general practitioner (GP). The skilled person will appreciate that any other health or fitness professional or the likes may take the place of a GP in alternative or additional examples, for example a Nurse, Physical Therapist, Consultant, Physician, Wellness or Fitness specialist. In this embodiment, the healthcare professional 9 can access the database means 7 via the access means 8 over the Internet via a web-based interface.

The connection 5, 6 between the manipulation means 4 and the database means 7 comprises a secure file transfer protocol connection, although any appropriate connection, secure or otherwise, could be used. The connection between the health professional 9 and the database means 7 is also a secure connection, using known secure Internet transfer methods such as SSL (Secure Socket Layer).

The body scanner 2 in one embodiment comprises a $NX_{16}$ white light scanner manufactured by $TC^2$. The scanner uses a plurality of white light sources to illuminate the person's body such that sensors can obtain measurements of the size and shape of the person for the generation of a three-dimensional model.

The body scanner 2 in another embodiment comprises a self-contained static laser, white-light or photonic 3D body scanner. The scanner uses a plurality of Image and Sensor sources to record the person's body such that sensors can obtain measurements of the size and shape of the person for the generation of a three-dimensional model.

Embodiments of the invention may take a pre-generated three-dimensional model of a person, generated by any suitable body scanner 2. The 3D model is used for the purposes of measuring part-volumes for the creation of a biomarker.

In alternative or additional embodiments, two or more photonic images (for example a front-view photograph and a side-view photograph, which may be taken using a hand-held mobile device or tablet 60) may be used to generate a 3D model of the subject for estimation part volumes instead of a more traditional body scanner 2.

In alternative or additional embodiments, multiple girth and length measurements may be combined to provide estimates of part volumes, instead of or as well as a camera, 3D scanner 2 or the likes.

The device 1 comprises processing circuitry arranged to perform the various processing steps. The manipulation means 4 and the body scanner 2 may each comprise some processing circuitry of the device 1.

In embodiments using measurements and/or images in place of a 3D scan, the processing to convert these data into a 3D model so as to extract volume information can be thought of as a 3D scanner. This may be performed, for example, online using software within a cloud-based system available to multiple users. Circuitry which performs the processing may be described as processing circuitry, whether or not it is a dedicated processing unit. The processing, and so the processing circuitry, may be distributed. The cloud software may be thought of as the "scanner" in such embodiments, as it effectively produces a 3D scan in a self-contained software environment.

The data collection means 3 comprises software loaded onto a computer that is connected to the scanner 2. The manipulation means 4 also comprises software loaded on to the same computer, wherein the manipulation software receives its input from the output of the scanner software 3. The manipulation software 4 includes a body volume calculator 11 and a health calculating device 19, both embodied as software in the embodiment being described.

The manipulation means 4 passes the data from the data collection means 3 to the body volume calculator 11 with any additional information, for example relevant to the health or medical history of a subject, as appropriate. For example, the manipulation means may specify for which body parts the volume calculator 11 should be calculated. The output from the body volume calculator 11 is passed to the health calculating device 19.

In some embodiments, the device 19 calculates a ratio between the first volume, corresponding to the first body part output by the volume calculator, and the second volume corresponding to the second body part output by the volume calculator. In alternative or additional embodiments, other combinations may be used instead of or as well as ratios, and/or one or more length measurements may be used in combination with one or more volume measurements in the generation of the biomarker.

The manipulation means 4 also receives input from body composition database means 51. The database means 51 contains information from medical surveys, for example, on the composition of people of different sizes, shapes, gender, ages and ethnicity. Thus, by comparing the information entered into the manipulations means 4 about the person being scanned and the measurements made from the three-dimensional model, the manipulation means 4 can extract the typical body composition for that person from the database means 51. As such, internal body composition data can be inferred for a subject for whom only external data has been provided, by comparison to other individuals in the database means 51 for whom internal data were provided (e.g. by way of MRI scans and/or cadaver data).

This information is used by the health calculating device 19, in combination with the ratio between the first and second volumes (or other combination of volumetric and length data) to generate the indication of a person's health, which may then be displayed. The indication of a person's health obtained can be used by the health professional to assess the person's health and the health risks to which they could potentially by prone. The healthcare professional can then recommend preventative measures, changes to diet, exercise or medication, surgery, or the like, to improve the health of the person scanned. The health indicator can therefore be used as a diagnostic tool, and/or optionally as a predictive health tool.

The manipulation means 4 also receives input from a feedback means 52 in the embodiment being described. The feedback means receives information entered by a health-care professional, for example, about any health problems that have developed in the scanned person. Such information can be used by the manipulation means to validate or improve the indication of a person's health initially calculated by the health calculating device 19. For example, if the indication of a person's health indicates that the person had a high risk of heart disease and subsequently that person developed heart disease, this information can be received by the feedback means 52. The health calculating device 19 may then (for example through predictive artificial intelligence or machine learning) alter an importance factor associated with the body volumes and/or lengths etc. it used to calculate the indication of a person's health, so that subsequent calculations of people with a similar size, shape or composition yield an indication of health that emphasises the health risk to a healthcare professional. The feedback means 52 therefore provides the device 1 with a means to validate and iteratively improve the accuracy of the results the health indicator device 19 produces.

The connection 5 may also be used to update the manipulation software 4 from a computer server (not shown) also connected to the Internet, or other network.

The manipulation means 4 is also connected to an output means 12, which comprises a printer in the embodiment being described. The printer 12 is arranged to print a datasheet 13, 50 showing at least the output from the manipulation means 4. In alternative or additional embodiments, the output means may distribute the datasheet and/or a BVI® value electronically, and/or present it electronically. In alternative embodiments, the output may be entirely electronic, for example a display on a screen, and a printer may not be present. Further, in some embodiments the output may be ephemeral—e.g. by being made visually available to the subject electronically and then deleted.

Details of a scanning method are provided in EP1993443 and U.S. Pat. No. 8,374,671; the skilled person is directed to these granted patents for further details. The contents of these patents are hereby incorporated by reference and the skilled person is directed to read these texts at least to understand an example of the generated outputs of part-volumes from a three-dimensional 3D scan.

Figure 6:
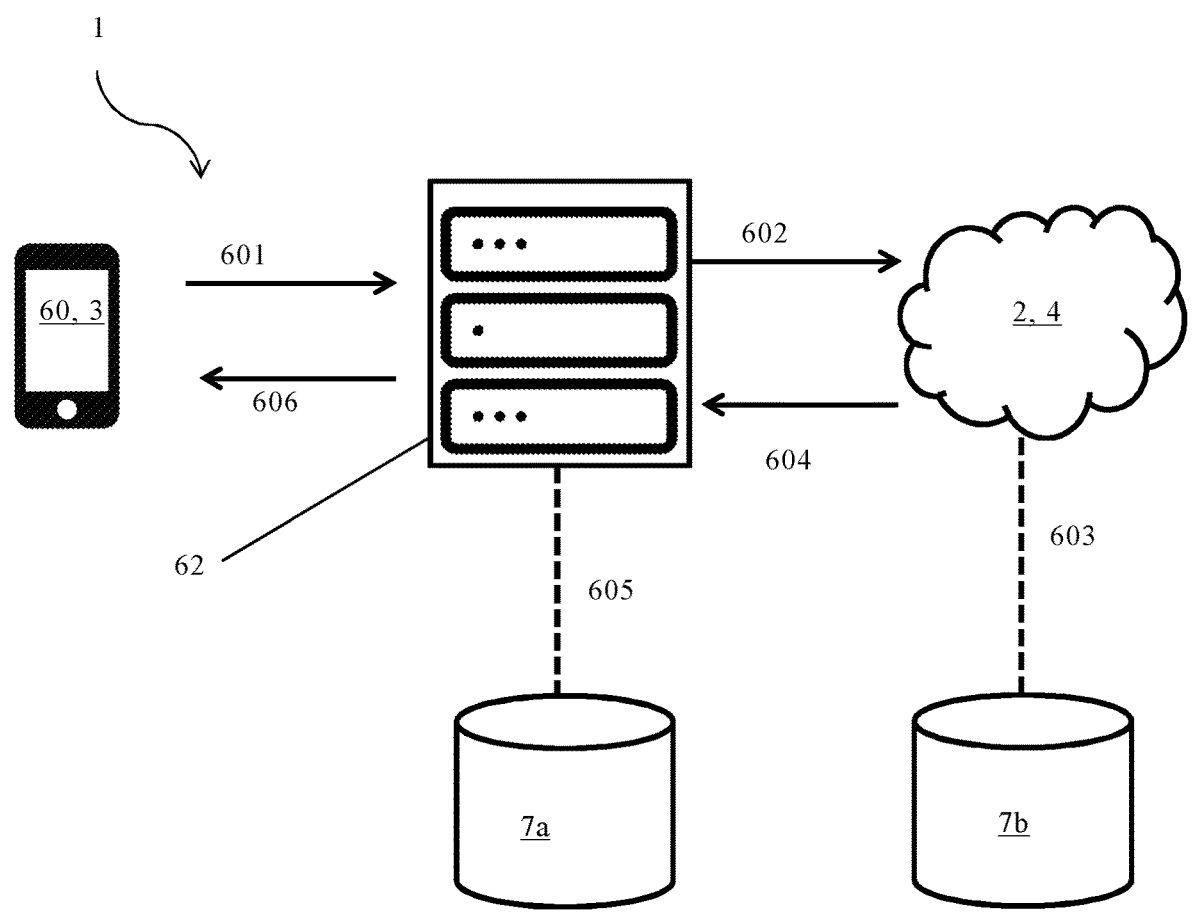
FIG. 6 shows a diagrammatic representation of a health indicator device suitable for calculating BVI® and optionally for use in determining an appropriate formula for the calculation of BVI®.

FIG. 6 shows a device 1 suitable for calculating the health indicator (a "health indicator device"). The device 1 may also be referred to as a system or network, as various components are physically separate, although able to communicate, in the embodiment shown. A smart phone, tablet or the likes 60 serves as a data collection means 3. In the embodiment being described, a subject takes two (or more) photographs of him or herself, using the smart phone 60.

In the embodiment shown in FIG. 6, the body scanner 2 and data manipulation means 4 are both provided by a cloud computing service 2, 4. The cloud computing service 2, 4 receives the photographs and generates a 3D body model from the photographs, thereby performing the role of a body scanner.

In the embodiment being described, the smartphone 60 is also used to input a client identifier (e.g. a username), one or more length measurements (e.g. height) and some basic personal information (e.g. demographic data such as age, gender and/or ethnicity). The skilled person will appreciate that relative measurements may suffice in some embodiments—in such cases, no length measurements or other data to provide a scale for the photographs may be needed.

The client identifier, photographs, measurements and basic personal information are then sent 601 to a BVI® server 62, for example over the internet. In alternative or additional embodiments, client information (e.g. demographic data, length measurements, and/or the likes) may be provided from a client server 7a instead of from the smartphone 60. In such embodiments, a client identifier (e.g. a username or unique reference number) may be provided via the smartphone 60 and corresponding data may be retrieved from the client server 7a for use, and/or the user may be prompted to supply any missing information.

In the embodiment shown, the BVI® server 62 is in communication with the client server 7a, such that data may be sent to, and retrieved from, the client server 7a. The client server 7a may store one or more of:

Client login data;
Personal data;
Historical data;
Photographs (optional); and
Body Volume, length and/or area data.

In the embodiment shown, the BVI® server 62 sends 602 the client identifier and basic personal information, the photographs and extracted measurements, to the cloud computing service 2, 4. The cloud computing service 2,4 then generates a 3D model from the photographs, extracts the measurements needed to calculate at least one of total body fat, visceral fat, and BVI®, and optionally also calculates BMI.

In alternative embodiments, the BVI® server 62 may generate the 3D model and extract one or more body part volumes, area measurements and/or length measurements and send those measurements to the cloud computing service, instead of leaving the 3D model creation to the cloud computing service.

In the embodiment shown, the cloud computing service 2, 4 is in communication 603 with BVI® server storage 7b. The BVI® server storage 7b comprises a database of anonymous body composition data (internal data, e.g. generated from MRI scans and/or cadaver data) and corresponding body shape data. The database optionally additionally comprises image storage.

The skilled person will appreciate that the internal data was taken into account when determining the formulae, and the coefficients of the formulae, to use for BVI®, visceral fat, and/or total body fat, and that, once the formulae have been established, access to the BVI® server storage 7b is not necessary. However, additional data may be added, and/or the formulae or coefficients thereof may be refined based on newly supplied data. In alternative embodiments, the generated 3D body model may be matched against the BVI® server storage 7b database to provide estimated internal data for the subject whose external data was used to generate the 3D body model.

In alternative embodiments, the cloud computing service 2, 4 may not be in communication 603 with the BVI® server storage 7b. The cloud computing service 2, 4 may receive the formulae (or the coefficients for a pre-programmed formula) to use from a different source, those formulae/coefficients having been determined using data in the BVI® server storage 7b previously.

Values for at least one of BVI®, total body fat, and visceral fat are then transmitted 604 back to the BVI® server 62 from the cloud computing service 2, 4. A BMI value may also be transmitted.

The BVI® server 62 provides the data (BVI®, total body fat, and/or visceral fat, and optionally BMI) as results to the subject, by transmission 606 to the smartphone 60, 3. In the embodiment being described, the values are colour-coded to represent a risk level (e.g. green for healthy, amber for be aware, and red for take action), and provided alongside recommended products, services, and/or actions. Optionally, feedback and user experience management content may also be provided, and user feedback may be sent from the smartphone 60, 3 back to the BVI® server 62.

The values may be provided without modification or other context in other embodiments.

In alternative embodiments, the roles of the BVI® server 62 and the cloud computing service 2, 4 may be provided by a single entity, and/or the BVI® server storage 7b may not be present, or may be combined with the client server 7a.

In alternative embodiments, any other suitable electronic device or devices may replace the smartphone 60, 3.

Figure 2:
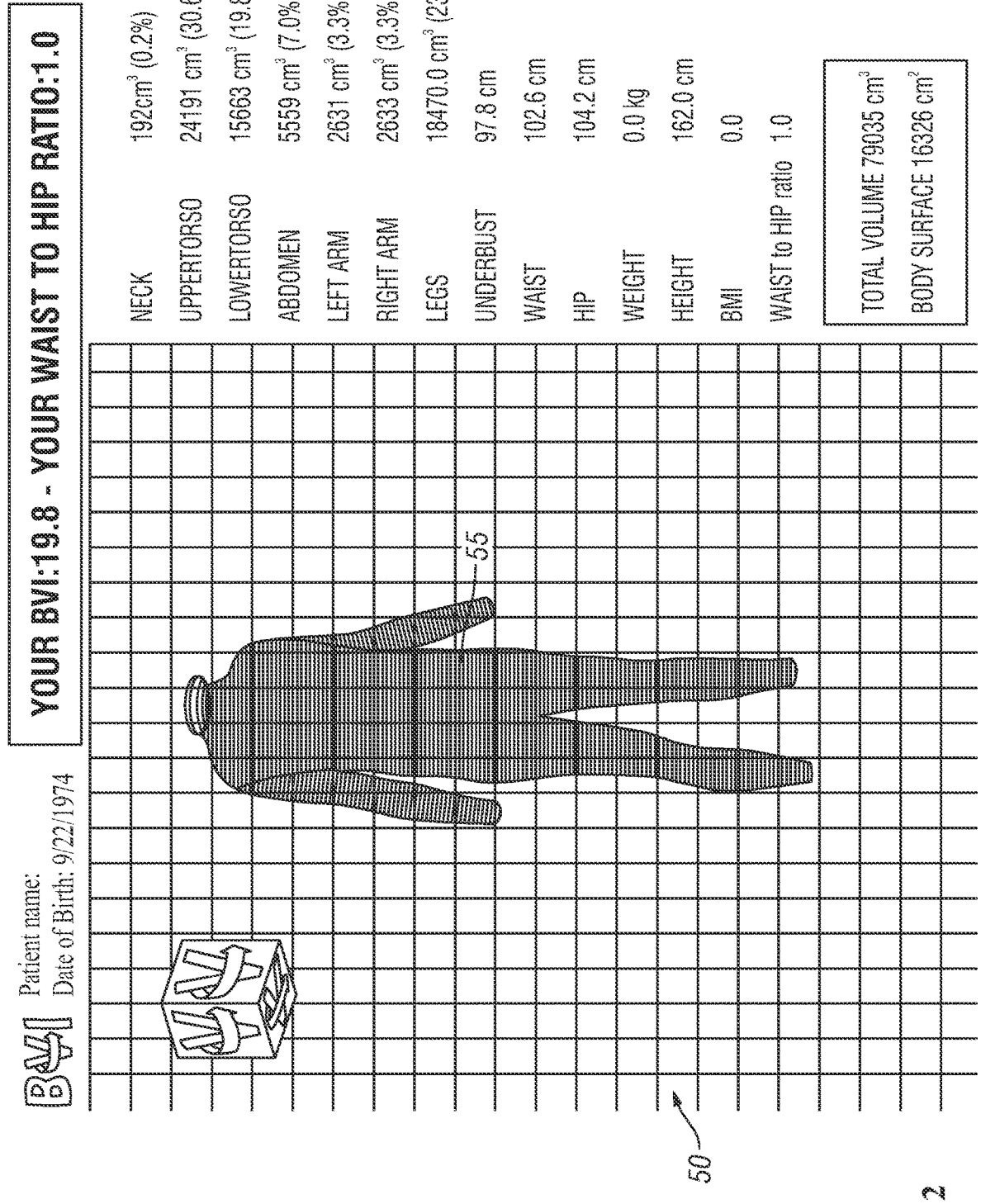
FIG. 2 shows an example of a BVI® datasheet.

FIG. 2 shows an example of a datasheet 50 printed by the printer 12. This datasheet shows a representation of the three-dimensional model 55 generated by the device 1. It also includes a plurality of measurements 56, some of which are calculated by the body volume calculator 11. In particular, the volume of the neck, upper torso, lower torso, abdomen, left arm, right arm, legs and total body is shown as calculated from the three-dimensional model obtained by scanning the person. The indication of a person's health is given as a figure labelled "BVI", which may be calculated using the ratios between the above-mentioned volumes.

The BVI® biomarker may be presented in the format of, or incorporated as, an ICD-10 code (10th revision of the International Statistical Classification of Diseases and Related Health Problems, a medical classification list by the World Health Organization) or CPT code (Current Procedural Terminology).

The BVI® biomarker may be displayed and/or stored in an ICD-10 or CPT code format, or encoded in any other appropriate manner.

The BVI® biomarker may be displayed in many different ways, for example on a health insurance certificate (hard copy or electronic copy), as part of client information for a client account with a health-related organisation, or the likes. Similarly, BVI® data may be stored and presented in internal records, such as those of a healthcare, health risk prevention, or health insurance firm.

In the embodiments being described, the BVI® is configured to provide an indication of the health risk or fitness of a person. Health risk may comprise one or more of the person's risk of Diabetes, High Blood Pressure, Liver Disease, Cancer, Obesity. Changes in a person's BVI® may also indicate improved health and/or fitness as compared to a previous record or assessment.

In the embodiments being described, the BVI® figure is a number. The skilled person will appreciate that letters, symbols or alphanumeric codes could be used to represent the numerical output of a BVI calculation (described below) in other embodiments.

In the embodiments being described, the BVI® figure is a single-digit or double-digit number, for example in the range of 0 to 99, and more preferably in the range of 0 to 20. In the embodiments being described, the BVI® figure has a decimal place following the single-digit or double-digit number. The skilled person will appreciate that other numbers and ranges may be used in other embodiments.

In the embodiments being described, the BVI® calculation uses volumetric measurements of a subject's body, including two or more of the volume (or at least a portion of any of the following volumes) of the pelvis, abdomen, chest, right arm, left arm, right leg, left leg and neck.

In various embodiments, in addition to part volumes (volumetric measurements of the human body), the BVI® calculation uses one or more of the following metrics:
  linear measurements of the human body;
  surface area measurements of the human body;
  body composition measurements of the human body (e.g. MRI data, Cadaver data, DEXA (Dual-energy X-ray Absorptiometry) data, or the likes giving a measurement of Visceral Fat and of Total Body Fat);
  social information about a human being or beings;
  demographic information about a human being or beings;
  physical attributes of a human being or beings;
  fitness and activity information about a human being or beings;
  dietary information about a human being or beings;
  medical information about a human being or beings; and
  reference information about a human being or beings.

The metrics listed above may be present in the data inputted by a subject and/or a healthcare professional, and/or in the constants used within the empirical formula used to calculate BVI® for a subject, the constants being calculated based on the above metrics extracted from the body database. Advantageously, in some embodiments the subject only has to enter external information such as height, weight, body part lengths and volumes and demographic information, and does not have to obtain measures of internal information such as body composition measurements. The fusion of internal and external data in the database may allow the empirical formula determined using the database to implicitly take predicted/expected internal information into account.

In the embodiments being described, the linear measurements comprise at least one of height, waist circumference, hip circumference, chest circumference, thigh girth, neck girth, bicep girth and leg length.

In the embodiments being described, the body composition measurements comprise at least one of body fat, visceral fat, liver fat, muscle, adipose tissue, fat free mass, subcutaneous fat and bone.

In the embodiments being described, the social information comprises at least one of home location, medical practice or hospital location, marital status, employment, background and lifestyle metrics.

In the embodiments being described, the demographic information comprises at least one of age, gender, ethnicity and socio-economic grouping.

In the embodiments being described, the physical attributes comprise at least one of physical height and weight.

In the embodiments being described, the fitness and activity information comprises at least one of number of steps taken, frequency of exercise, level of physical activity and attitudes to fitness and activity.

In the embodiments being described, the dietary information comprises at least one of type of food eaten, volume of food eaten, time of day eaten, types of diets undertaken, food allergies, and attitudes to food.

In the embodiments being described, the medical information comprises at least one of previous medical history, medical conditions recorded, blood test results and genetic pre-conditions and risk elements.

In the embodiments being described, the reference information comprises at least one of a Patient ID number, a Client ID Number, a National Health Service (NHS) Reference Number, Oxford Innovations or American Heart Association health outcomes reference, or any other Unique Identifying number, letter or other designation used as a reference. For example, any designator familiar to a healthcare professional or other health related organisation may be used.

In addition, a BVI® designation for the subject may also be used. BVI® designation means the BVI® number assigned to the individual, as calculated using the methods described herein. The BVI® designation may be encoded or presented in such a way as to include information allowing the subject to be identified in some embodiments.

Some or all of the metrics above for a plurality of people are stored in a body database in the embodiment being described. In some embodiments, the body database is used to collect aggregated data statistics, which may then be stored in a separate database (optionally anonymised).

Data 502, 504, 506 stored in the body database are used to define first and second empirical formulae 510 for predicting Visceral Fat and Total Body Fat (internal body composition data) 520 based on external 514 and demographic 512 information.

The data 502, 504, 506 stored in the body database are used to define a third empirical formula 510, the output of which is the BVI® 520, and is configured to give an indication of health risk, and in particular of obesity and cardio-metabolic risk. As these are correlated to Total Body Fat and Visceral Fat, the BVI® therefore provides a measure of Total Body Fat and Visceral Fat, i.e. internal body composition data, whilst requiring only external and demographic data from a subject. The need for costly, time-consuming and potentially-daunting MRI scans or the like to obtain a general health indicator may therefore be reduced or eliminated for the subject by the use of BVI®.

Figure 5:
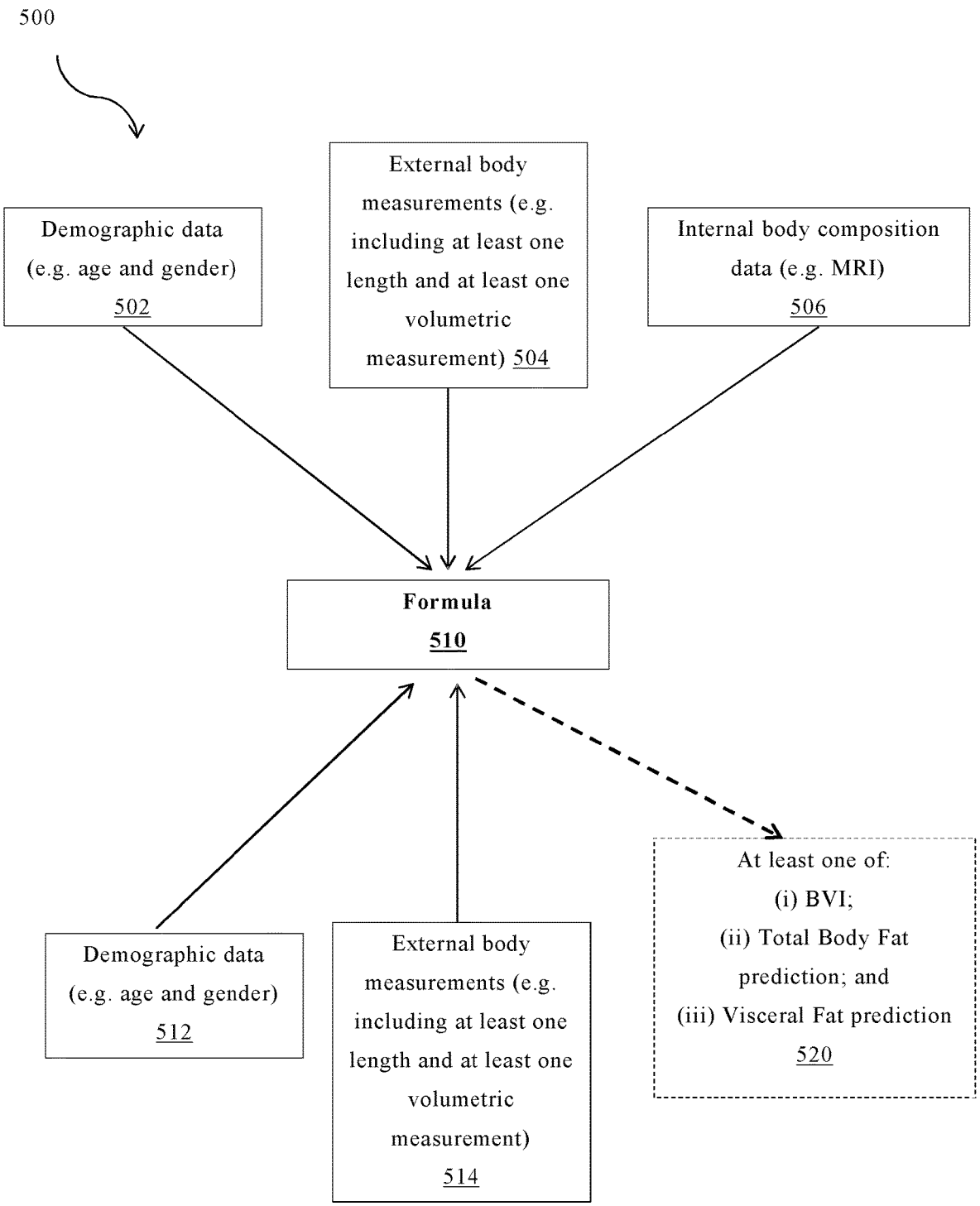
FIG. 5 shows a summary of the processes shown in FIGS. 3 and 4.

This process 500 is summarised in FIG. 5

In these embodiments, the BVI® is configured to provide an indication of the health or fitness of a subject.

In these embodiments, the BVI® is calculated and assessed by combining data on the subject with data on other people stored in the body database so as to (implicitly or explicitly) extract a typical body composition for the subject from the body database, based upon body volume calculations, and then calculating an indication of health risk accordingly. In some embodiments, predicted Total Body Fat and/or Visceral Fat may be calculated and used as inputs to the BVI® formula.

During extensive, independent scientific and medical evaluation of part body volume measurements, a variety of possible indices were investigated as suitable candidates for, or components of the BVI® biomarker:

Possible Volume Indexes

Volumes (Body Part Volumes)

1. Chest
2. Abdomen

3. Pelvis
4. Upper limbs
5. Lower limbs
6. Neck

Circumferences (Body Length Measurements)

A. Waist
B. Hip
C. Neck (circumference and height *)
D. Arm (mid point)
E. Thigh (mid point)
* Neck Height from the ground Possible Body Volume Indexes Circumference Indexes Index=(1+2)/Total Volume Index=$A/B$ Index=2/Total Volume Index=$A$/height Index=$A$/height$^3$ (the superscript indicating that height is squared)

Index=(1+2)/(4+5)

Index=$(A+C)/B$

Index=2/3

Index=$(A+C)/(B+E)$

Index=Total Volume/height

Index=Total Volume/height$^2$

Index=$C/B$

Index=Total Volume/height$^3$

Index=$C/B+E$

Index=(1+2+6)/Total Volume

Index=$1/(B$/height)

Index=(2+6)/(3+5)

Index=$1/(B$/height$^2$)

Index=(2/Total Volume)/height

Index=(2/Total Volume)/height$^2$

Index=(2/Total Volume)/height$^3$

Index=2/height

Index=2/height$^2$

Index=2/height$^3$

Medical data from over 7,800 patients who had also undertaken a 3D scan in a body scanner 2 was analysed against the prospective 15 indices to establish which was the most appropriate and significant one for an assessment of risk. Regressional analysis allowed suitable candidate indices for BVI® to be identified.

Following completion of that appraisal, it was established that two effective and appropriate measures of risk using part volumes were:
1. Abdominal Volume as a proportion of Total Body Volume; and
2. Abdominal Volume and Leg Volume as a proportion of Total Body Volume.

External measurements (length and volume measurements) in conjunction with full-body MRI scanner data and demographic information for the same people was subsequently used to validate the determined indices. This further validation augmented and supplemented the validation of volumes to create a 'synthesis' and fusion of two (or more) distinct datasets, allowing linear, volumetric and MRI data to become used and validated for the first time. In the embodiment being described, the different datasets comprise data on the same subjects. Linear, volumetric, MRI data and reference to existing known biomarkers such as Cholesterol and Glucose derived from the subject blood results were used and validated in the creation of a BVI® biomarker as a predictive indicator of health risk.

The third empirical formula was adapted to include modifications according to demographic information such as age, ethnicity and gender in addition to the external body data.

Over 15 different indices of body volume parameters were reviewed against known indicators of obesity and cardio-metabolic risk. In one embodiment, a combination of total body volume and volume of the abdomen was selected as providing the best combination of measurements for the enrichment of current cardio-metabolic risk prediction methods, and is used for the BVI® calculation, optionally with height, weight, and/or gender also used.

In another embodiment, the following equation is used to calculate BVI®:

$$BVI=u-v^*(\text{abdominal\_volume\_litres}/(\text{height\_metres}^*\text{height\_metres}))-w^*\text{age\_years}-x^*\text{gender}+y^*\text{height\_metres}-z^*\text{waist\_girth\_cms}$$

Coefficients u to z in the equation above are constants derived empirically from data in the body database.

The skilled person working in the field will appreciate that average body shapes vary for different populations throughout the world, for example when comparing Asian populations to European populations or to African populations, or even comparing north-eastern European to southern European populations. The coefficients (u to z, or equivalent for other embodiments) are therefore adjusted based on data for the population of interest in various embodiments, so as to provide a more accurate health indicator, accounting for genetic and/or cultural variation in body shape.

In a similar way, this fusion of internal and external data in the body database was used to generate the first and second empirical formulae, such that Total Body Fat and Visceral Fat predictions can also be made from just external data (e.g. one or more of height, weight, body part volumes and/or lengths, etc.) and demographic data (e.g. one or more of age, gender, ethnicity, activity level, etc.). The fusion of internal body composition data (e.g. MRI and/or Cadaver data) and externally derived 3D body part data (lengths and volumes) to form the formulae facilitates this prediction.

The skilled person will appreciate that the number of different parameters of the BVI®, Total Body Fat and/or Visceral Fat, or the likes, determination approaches may be increased to increase accuracy, but that this put more of a burden on the subject in terms of supplying relevant information. A trade-off between accuracy and simplicity of use can therefore be struck according to intended use. The skilled person will appreciate that, for BVI® to be a useful alternative to BMI, it has to be similarly available and deployable as a quick, efficient and valid tool.

Figure 3:
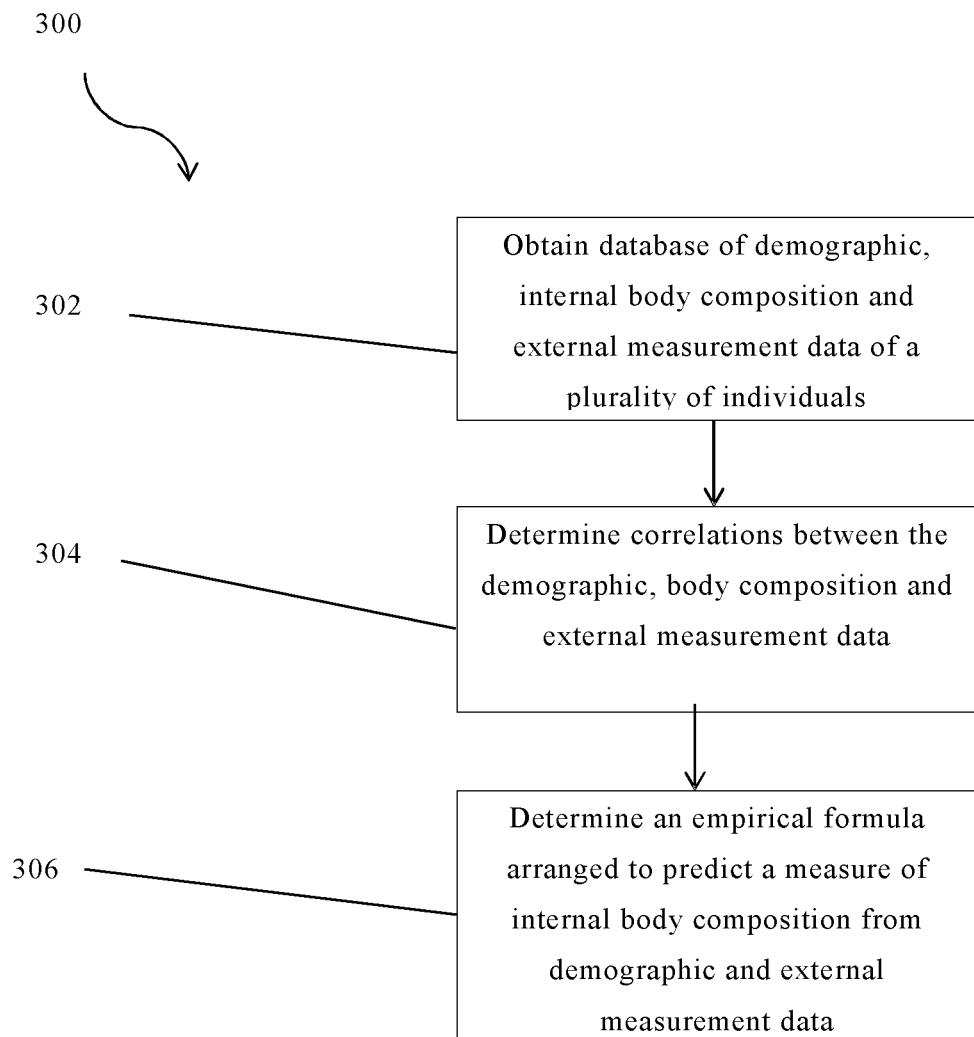
FIG. 3 shows a flow chart of a first method of determining empirical formulae to output the desired values.
Figure 4:
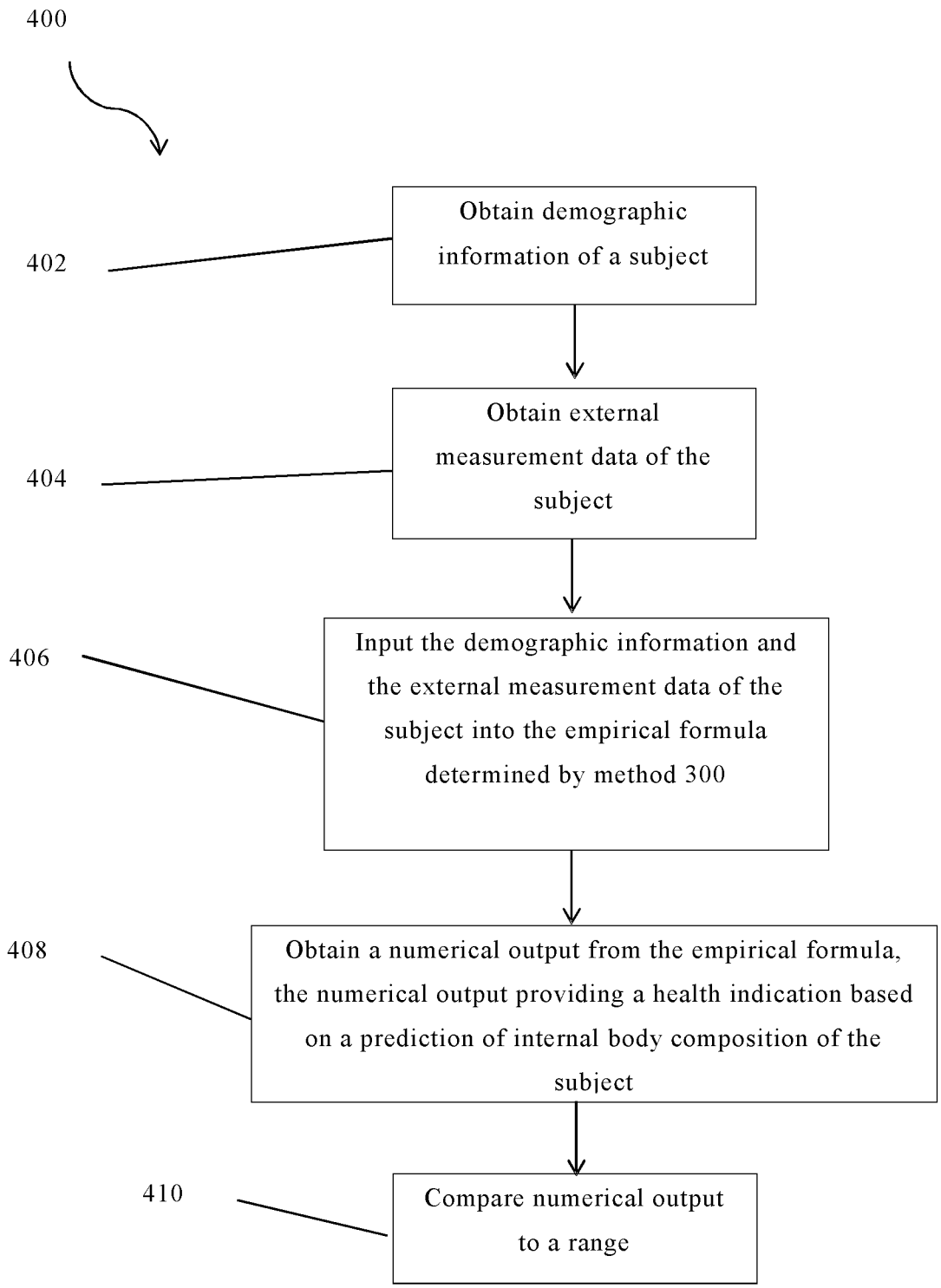
FIG. 4 shows a flow chart of use of the empirical formulae in providing a diagnostic tool.

This method 300 is summarised in FIG. 3. Firstly, data are obtained 302 including some or all of the information and measurements discussed above and optionally additional metrics known to provide health indications (for example, visceral fat content as obtained from MRI data), as well as demographic data of the individuals whose data are included. Then, relationships between the various metrics are investigated so as to find correlations 304.

Based on these relationships, the empirical formulae which provide a prediction of internal body composition from external data (such as 3D images and a 3D model formed therefrom) and demographic data are then determined 306. Multiple external and demographic metrics are used with the intention of overcoming some of the drawbacks of prior art metrics such as Body Mass Index, which does not take into account body shape at all, nor whether mass is a result of muscle or fat.

The measure of internal body composition can be or comprise a direct measure such as Total Body Fat or Visceral Fat, and/or may be or comprise an indirect measure including multiple factors to provide a health indication, such as BVI®.

In the embodiments being described, the BVI® number provides an indication of the scale of the health risk or fitness of a person, by reference to a series of ranges.

In one embodiment, the BFI® number is defined as being from 0-20, with four numerical sub-ranges (0-<5, 5-<10, 10-<15, and 15-20). The skilled person will appreciate that the total available range could be sub-divided into more or fewer sub-ranges for comparison, and/or that the total range of BVI® may be different, including the option of being unlimited, in other embodiments.

The principle of BVI® is to establish a new Health Indicator based upon weight distribution (as opposed to total weight and total height only); delivered through the measurement of part-volume of the human body from a 3D scan or equivalent.

Summarised below is the process undertaken in the development of the body volume technology in order to establish a preferred BVI® "number" and an appropriate series of ranges for that number:

STAGE 1—Desk research and analysis of MRI full-body data;
STAGE 1b—Validation and confirmation of accuracy levels of BVI® software for part volume measurement, including validation for total body volume against BodPod®;
STAGE 2—Desk research and analysis of cadaver data;
STAGE 2b—Validation and confirmation of accuracy levels of BVI® software for body composition;
STAGE 3—Trials of body volume 3D software with MRI data using the same subjects;
STAGE 3b—Validation and confirmation of accuracy levels of BVI® software for body composition;
STAGE 4—Overall review and analysis of data outputs from Stages 1-3;
STAGE 5—Trials of linear 3D software with manual measurements using same subjects; and
STAGE 6—Review of data and devising of algorithms for the BVI® number and ranges.

Having reviewed the 15 possible indices discussed above, it was decided to adopt and use abdominal volume as related to total body volume as the primary basis for the BVI® calculation. Weight distribution was measured using the part volume 3D calculations, enhanced and adjusted by reference to cadaver data to include the ratios between weight and volume of different body parts within each body section.

In view of this, certain definitions and ranges for abdomen volume were established, using the extensive 3D datasets. These ranges were defined (and written in language for the healthcare professional) as being as listed below in one embodiment. The skilled person will appreciate that this is an example only, and that other ranges and definitions may be used.

Abdomen Volume

The BVI® technology allows, for the first time, the measurement of the abdominal region of the body; the area of the body where excess weight is most commonly associated with health risk. Whilst excess abdominal volume in a subject is visible to the human eye, prior health indication techniques cannot extract and remove the abdominal volume from the body in practice; other than by cadaver dissection after a patient has passed away. Extraction of part volumes, including volume of the abdomen, from a 3D model, and use cadaver and MRI data as empirical reference data to interpolate body composition of the abdomen and other part volumes therefore provides a novel and beneficial approach.

For the purposes of the calculations described herein, the abdominal region is defined as being broadly measured from the bottom of the ribcage to the pelvic bone, and more specifically to the top of the pelvic bone; the iliac crest. This entire area is what is more commonly known as the 'belly' or the 'stomach' which is the part of the body where excess fat deposits, such as visceral fat located around the organs, can cause health problems and are generally thought to be most indicative of potential health issues. The exact abdominal volume calculated as a proportion of total volume may be different according to different body shapes of subjects (e.g. hourglass, pear-shaped, apple-shaped), but the software has been designed to capture the area of an individual that might reasonably be thought of as their 'belly'. The importance of this is that a subject with a 'pot belly' will have the entire abdominal volume measured using BVI®, including the area just above the groin. This area of the body is generally neither practical nor appropriate to measure manually.

During the image capture process (which may be 3D or 2D image capture), a patient or client is advised to breathe out and hold their breath for about 5-6 seconds as the image is taken. The BVI® software will measure the abdomen as a proportion of the total volume (less head, hands and feet in the embodiments being described). The head is excluded as the volume of hair is not a health issue; nor do people who have big feet or large hands have a greater or lesser health risk.

The volume of the abdomen is also indicative of amounts of visceral fat deposited within the body. Visceral fat is known to be relevant to health. Visceral fat, located around the major organs, is known to be relevant and a significant indicator to health risk.

Ranges for Abdomen Volume (Same for Both Male and Female)

Below 5.00%

If the abdomen volume is below 5%, then this could be indicative of a subject's low total body volume, a specific body shape (e.g. 'hourglass') or may be reflective of other health issues which require further consultation. It is very unusual for the abdomen volume to be less than 5% of the total weight. Therefore in this case, the Physician or Healthcare Advisor should give advice to the subject taking other data from the BVI® technology and other factors into account.

5.0%-9.9%

Within this range, the subject has a low level of abdomen volume which is indicative of a healthy body shape and health risk. The Physician or Healthcare Advisor should offer advice to the subject taking other data from the BVI® technology and other factors into account if that is deemed to be necessary.

10.0%-14.9%

Within this range, the subject has an average level of abdomen volume which is indicative of a healthy body shape and health risk. The Physician or Healthcare Advisor should offer advice to the subject taking other data from the BVI® technology and other factors into account if that is deemed to be necessary.

15.0%-19.9%

Within this range, the subject has a relatively high level of abdomen volume, which is indicative of a less healthy body shape and health risk. The Physician or Healthcare Advisor should offer advice to the subject taking other data from the BVI® technology and other factors into account if that is deemed to be necessary.

20%-24.9%

Within this range, the subject has a high level of abdomen volume relative to total volume, which is a sign of potential health problems and health risk. The Physician or Healthcare Advisor should offer advice to the subject taking other data from the BVI® technology and other factors into account to provide the subject with appropriate exercise and diet programs. This will help the subject to reduce their abdominal weight and improve their health.

25.0%-29.9%

Within this range, the subject has a very high level of abdomen volume which is indicative of health risk and possible excess visceral fat in the abdomen. The Physician or Healthcare professional should review all other factors and suggested appropriate remedies and programs appropriate to the needs of the subject to improve their health.

Having defined the ABDOMEN VOLUME the VISCERAL FAT and TOTAL FAT RANGES are now described. These are detailed below for one embodiment:

Total Body Fat Ranges (as Written for a Healthcare Professional)

Women

Range Between 5% and 11%

The body fat percentage (BFP) for males and females is the total mass of fat divided by total body mass; body fat includes essential body fat and storage body fat. Essential body fat is necessary to maintain life and reproductive functions. The percentage of essential body fat for women is greater than that for men, due to the demands of childbearing and other hormonal functions.

This subject has a very low fat content in their body which is good for their health, but some fat in the body is essential for healthy living. The healthcare professional could advise the subject to begin a program that is appropriate for them, if that is required or if the situation changes.

Range Between 11% and 22%

This subject has a relatively low amount of fat in their body but this may increase if their lifestyle changes or their dietary requirements worsen. The subject should keep to the same lifestyle and levels of exercise that they are currently doing. However, the subject could be advised to begin a program that may be appropriate for them if that is required or if the situation changes.

Range Between 22% and 28%

Body composition constantly changes and comparing ratios over time is only relevant as a broad indicator of how healthy a subject's weight is. The figure given determines the level of fat, but doesn't indicate the position of the fat on the body, or its potential implications.

A normal body composition does include some essential fat, but beyond a certain percentage, the subject may be at risk of weight-related diseases such as diabetes and heart problems.

By tracking BVI® over time, the subject's progress can be tracked to see if any improvements they are making to their physical activity and diet are making an impact on their physical condition and weight.

The subject has no need to be concerned or anxious, but they have a relatively high level of total body fat, which could affect their mood. It is important to inform the subject that they should not increase their body fat percentage above these levels and offer advice to begin a program, appropriate for them, which will help to avoid an increase in their body fat levels.

Range Between 28% and 38%

This subject has a high body fat content, so it is important to determine whether the fat is subcutaneous or visceral. A high level of subcutaneous fat is not a health risk for the subject, whereas a high level of visceral fat means the opposite; hence the importance of weight distribution measured through part volumes which allows the location of fat, as opposed to total fat, to be realised and represented for the first time through BVI®.

Tracking a subject's body fat percentage is an accurate measurement of their health and fitness, but it is more relevant for health risk to measure their visceral fat percentage, so BVI® data can offer guidance on risk and help with their personal health goals.

The level of the subject's visceral fat can be checked against the BVI® chart ranges. If required, the healthcare professional can advise the subject to begin a program that is appropriate for them or as and when the situation changes, or conversely, a subject may appraise themselves of their own situation and seek advice or make their own plans accordingly.

Range Between 38% and 48%

For women, the general body fat range is anywhere between 14% and 31% and at least 10% body fat is required to be healthy. A woman with more than 32% body fat is considered obese. This subject has a high level of body fat so should be advised to take action to reduce this where possible.

There could be any number of reasons why this is the case so after an assessment of the subject, a specific program that will be appropriate for their specific circumstance can be recommended.

Range Over 48%

If the subject has a body fat range in excess of 48%, then this is a potential health risk as the percentage of body fat is likely to include excess visceral fat in addition to the essential subcutaneous fat. An excess amount of visceral fat is considered to be a potential health risk and specific advice should be provided to a subject that has been assessed as having this amount of total fat.

Men 3-23%

If a man's body fat is less than 3%, his health may be compromised because normal, healthy functioning requires some essential subcutaneous fat. He may become more susceptible to illness or experience chronic fatigue. 3% of body fat is considered to be essential for men as some fat is necessary for normal, healthy functioning.

In men, essential fat is approximately 3% of body weight. Women, however, have a higher percentage of essential fat—about 12%, due to essential fat found in the breasts, pelvis, hips and thighs. This sex-specific fat is believed to be critical for normal reproductive function.

Visceral, or storage fat accumulates beneath the skin, in certain specific areas inside the body, and in muscles. It also includes the deep fat that protects internal organs from injury. Men and women have similar amounts of storage fat.

The subject does have a low volume of fat but nothing so low to raise concerns. The subject could be advised to begin a program that is appropriate for them, if that is required or if the situation changes.

23%-34%

If the subject's percentage body fat goes above a desirable range, they have an increased risk of developing heart disease, high blood pressure, gallstones, type 2 diabetes, osteoarthritis, certain cancers and for an early death. In some cases, the excess fat becomes a mechanical barrier to breathing properly. This condition is called sleep apnea.

BVI® can inform a health professional and the subject where any excess fat is located, which is important. Recent studies have shown that there is a higher risk associated with carrying extra fat around the waist, rather than the thighs and buttocks, which can be healthy.

It will benefit the subject's health if they can maintain a healthy weight and to keep body fat in check, improving longevity and quality of life.

Within this range, the subject has no need to be concerned or anxious. The healthcare professional could offer advice to begin a program, appropriate for them, which will help avoid an increase in their body fat levels.

34%-40%

Studies show that maintaining a healthy weight compared to height reduces risk and being obese increases risk. People with excess body fat are more likely to eat a diet high in fat content—with less fruit & vegetables, so they may be missing out on essential nutrients. The subject's total body fat percentage does indicate a certain level of concern, but the fat type remains the most important factor. The subject's visceral fat levels and abdominal volume should be utilised as a better indicator to determine the level of risk and any action required.

If appropriate, the subject could be made aware that this result is a cause for concern and if required, advised to begin a program that is appropriate for them or as and when the situation changes.

40%-46%

Within this range, would exist a high propensity and risk for Type II Diabetes and sufferers of Type II Diabetes should be advised to eat healthily and try to maintain a healthy weight for their height. A balanced diet with plenty of fruit and vegetables, and the bulk of starchy foods, means that the type II diabetic can consume a small amount of sugar—and foods containing sugar can be included (on a small scale) in the day to day diet.

For a subject within this range, their total body fat volume is concerning and will indicate a tendency of additional abdominal volume and the associations with the volume of visceral fat. The subject's visceral fat levels should be checked and they should be advised to begin a program that is appropriate for them and which will help them avoid an increase in their body fat levels.

Over 46%

For men, the general body fat range is anywhere between 6% and 25% and at least 3% body fat is required to be healthy. A man with more than 26% body fat is considered obese. This subject has a high level of body fat so you need to advise them to take action to reduce this where possible.

This total body fat poses a health problem for your client as excess body fat contributes to an array of medical conditions/diseases. Not maintaining a healthy weight for their height can greatly increase their risk of contracting conditions such as Coronary Heart Disease, Diabetes, some Cancers and other conditions such as Gallstones. The visceral fat indicator of body volume is likewise a representation of the risk factors involved.

The healthcare professional should provide specific advice to a subject within this range to begin a program that is appropriate for them and to improve their health.

Finally, having assessed and delivered both indicators and ranges for ABDOMEN VOLUME, VISCERAL FAT and TOTAL BODY FAT ranges, the final stage was establishing a 'range' for the BVI® number to correspond to the existing BMI scale. The skilled person would appreciate that an entirely different scale could be chosen in some embodiments, but that aligning the scale for BVI® with that for BMI makes the numerical system more familiar and easier to understand for users familiar with BMI as an indication of a risk to health.

For the representation of BVI®, it was decided to use a range of between 0 and 20, so as to 'tag on' to the most commonly used lower-range BMI numbers and also to create a structure of 5-digit ranges; familiar to anyone who is using, has used, or is familiar with the BMI number and its most commonly used ranges of 18-35 in a two-digit format.

Visceral Fat

These are detailed below, with ranges reviewed and validated as being scientifically representative by renowned experts in the field. The representation of the values in pounds is indicative of what is deemed appropriate for the US population, but likewise, may also be appropriate to be represented in litres, as a percentage or other known value, as appropriate to the accepted norms and measurement values as used in any given population.

Women

Range Between 0.22 and 3.3 Pounds (0.5 kg to 7.3 kg)

Within this range, this subject has a very low visceral fat content. Advice should include avoiding overfeeding, particularly if the subject has a low-activity lifestyle. A healthcare professional could advise the subject to begin a program that may be appropriate for them if that is required or if the situation changes.

Range Between 3.3 and 6.6 Pounds (7.3 kg to 14.5 kg)

Fat is a living part of the body; releasing chemicals, toxins and hormones into the blood stream which can affect many bodily functions. This subject has a relatively low amount of visceral fat but could be advised to begin a program that may be appropriate for them if there are other factors that may indicate a need to do so.

Range Between 6.6 and 11.0 Pounds (14.5 kg to 24.2 kg)

Visceral fat can affect mood of human beings by increasing production of Cortical (stress hormone) which reduces levels of endorphins. This subject has a relatively high level of visceral fat and it is important that this should not increase. The subject could be advised to begin a program appropriate for them.

Range Between 11.0 and 15.5 Pounds (24.2 kg to 34.1 kg)

There is evidence that visceral fat causes inflammation in the colon and the artery walls and is a major cause of heart disease, diabetes and some types of cancer. This subject has a high level of visceral fat and should take some action. The subject could be advised to begin a program appropriate for them.

Range Between 15.5 and 20.0 Pounds (34.1 kg to 44 kg)

Subjects within this range have a very high level of visceral fat in their body and therefore must start to move often and adopt a healthy lifestyle to reduce this. A healthcare professional should advise their client to begin a program appropriate for them.

Men

Range Between 0.22 and 5.5 Pounds (0.5 kg to 12.1 kg)

There is evidence that visceral fat burns away uniformly with exercise. This subject has a very low visceral fat content and presents with little risk. The subject could be advised to begin a program appropriate for them if that is required or if the situation changes.

Range Between 5.5 and 10 Pounds (12.1 kg to 22 kg)

Any subject within this range has a relatively high level of visceral fat and needs to take evasive steps to manage their lifestyle and the causes of visceral fat. It is important to note that appearance is unrelated to the levels of visceral fat. This is commonly known as a 'TOFI' body type—thin on the outside, but fat on the inside. A healthcare professional should advise the subject to begin a fitness and exercise program appropriate for them to help manage this situation and reduce their visceral fat volume.

Range Between 10 and 13.25 Pounds (22 kg to 29.2 kg)

The liver metabolises visceral fat and then releases it into the bloodstream as cholesterol. Low-Density Lipoprotein (LDL), commonly known as 'bad cholesterol', builds up into a plaque that blocks the arteries. An increase in fat carried on the body, causes an increase in harmful toxins which are released into the bloodstream and stored in the body. Any man within this range is carrying a significant amount of visceral fat and the healthcare professional should advise the subject to begin a program appropriate for them to help manage this situation and reduce their visceral fat volume.

Range Between 13.25 and 20.00 Pounds (29.2 kg to 44 kg)

It is not necessary to be overweight to have a large amount of visceral fat. There are case histories of underweight individuals who have up to 15 pounds of hidden visceral fat. This is commonly known as a 'TOFI' body type—thin on the outside, but fat on the inside. A subject in this range is carrying a significant amount of visceral fat and should be advised to begin a program appropriate for them to help manage this situation and reduce their visceral fat volume.

Range Between 20.00 and 28.5 Pounds (44 kg to 62.7 kg)

This range represents a very high level of visceral fat and should be addressed to protect long-term health and well-being. The subject should be advised to begin a program appropriate for them to help manage this situation and reduce their visceral fat volume.

The explanation for the BVI® number is included in this text with the set ranges within which a specific designated number for any given subject may lie. The empirical formula, combining height, weight, gender; total body volume and volume of the abdomen as chosen for the BVI® calculation of the embodiment being described, is scaled to provide values within this range as appropriate.

Ranges for the BVI® Indicator Number (As described for a healthcare professional representing or being asked to advise a subject on their health)

The Body Volume Indicator (BVI®) has been developed over years of research by Select Research and collaborators. The BVI® of the embodiment being described derives total body volume, less the head, hands, and feet (for example from two digital images, or from a 3D scan if available) that then is divided into seven body part volume sections; Chest, Abdomen, Pelvis, Left Arm, Right Arm, Left Leg, Right Leg.

The empirical formula combining height, weight, gender; total body volume and volume of the abdomen was selected to represent BVI® following an appraisal and evaluation of 15 part volume equations. For the BVI® index, calculation is scaled to provide values within this range as appropriate.

Ranges

BVI—0-4.9

A subject within this range has a very low BVI® number may put them at low risk of developing cardio-metabolic disease. The abdominal volume in proportion to the total volume is adequate. However, a healthcare provider should still review other risk factors and provide advice on how to continue with a healthy diet and lifestyle.

BVI—5.0-9.9

The subject's BVI® number may indicate that they are at low to medium risk for cardio-metabolic disease, as a result of their abdominal volume being higher in proportion to their overall total body volume. However a healthcare provider should still review other risk factors and provide advice on how to continue with a healthy diet and lifestyle.

BVI—10.0-14.9

The subject's BVI® number is indicative of them being at moderate risk for developing cardio-metabolic disease, as their abdominal volume is high in proportion to their total body volume. However a healthcare provider should still review other risk factors and provide advice on how to continue with a healthy diet and lifestyle.

BVI—15.0-19.9

The subject's BVI® number may be indicative of a high risk of developing cardio-metabolic disease, as their abdominal volume is high as a proportion of their total body volume. However a healthcare provider should still review other risk factors and provide advice on how to continue with a healthy diet and lifestyle.

In various embodiments, the Body Volume Indicator is collected and displayed on a smartphone by the use of two digital images through the BVI® Pro iOS app; specifically designed for healthcare professionals. The BVI® Pro, which includes the BVI biomarker number was launched on May 1, 2017. In addition, BVI® has been approved as a 'medical device' by the Medical Healthcare Evaluation Authority (MHRA), confirmed as being classified 'general wellness' product for the Food and Drug Administration (FDA) and has been CE Marked across Europe.

Since the launch in May 2017, the BVI® Pro has been used for the measurement of subjects in over 67 countries across the world by users. The launch of the BVI® Image Application Programming Interface (API) in April 2018, which includes the BVI® algorithms as described above, is intended to further enhance the opportunities for integration of the BVI® biomarker in healthcare. The increased use of BVI® across the world by healthcare professionals, health and wellness companies and by individual subjects can only assist us in better understanding, monitoring, evaluating and improving the health of our nations and their citizens.

What is claimed is:

1. A system for performing a series of steps so as to provide a health indicator of an individual human being, the system comprising:
    (a) a camera operating on a first computing device, and arranged to capture at least two unique digital photographs of the individual, wherein the at least two unique digital photographs include a front-view image and a side-view image;
    (b) a data collector operating on a second computing device, and arranged to, after the at least two unique digital photographs are captured, receive the at least two unique digital photographs and demographic information of the individual from the first computing device via an internet connection, using a secure file transfer protocol connection, wherein the demographic information includes gender, and after receiving the at least two unique digital photographs, extract linear measurements indicative of body shape from the at least two unique digital photographs as received from the camera; and
    (c) a calculator, configured to:
        electronically receive the measurements and the demographic information from the data collector and generate a 3D model of the individual using the received measurements extracted from the captured at least two unique digital photographs;
        after the measurements and the demographic information are received, retrieve information from a body composition database, the body composition database comprising internal body composition data and corresponding body shape and demographic data of other individual human beings, the retrieved information being selected based on identifying a subset of data in the database based on the received demographic information, and matching the measurements received from the data collector to body shape data in the identified subset of data in the database;
        after retrieving the information, determine a value for the health indicator by automatically synthesizing the measurements received from the data collector and the retrieved information from the body composition database; and
    return the health indicator value and the 3D model to the first computing device for display on a screen of the first computing device.

2. The system of claim 1 wherein the calculator calculates multiple body volumes of body parts of the individual.

3. The system of claim 1 wherein the data collector further measures at least one of: a girth measurement, a length measurement, and a surface area measurement.

4. The system of claim 1 further comprising:
    (d) a first database comprising measurements obtained based on the at least two digital photographs and configured to be accessed via the internet connection.

5. The system of claim 4 wherein the first database further comprises supplemental health information for the individual provided by at least one of a third party and the individual human being.

6. The system of claim 1 wherein at least one of the data collector and the calculator is provided by a cloud-based analysis system.

7. The system of claim 1 wherein the calculator is configured to calculate a first body volume of a first body part and compare it to a second body volume from a second body part.

8. The system of claim 4 further comprising:
   (e) a second database comprising the body composition database, accessed via the internet connection,
   (f) means to compare values in the first database to values in the second database.

9. The system of claim 1 wherein the received demographic information and the demographic data of other individual human beings further comprises at least one of an age or an ethnicity.

10. The system of claim 1 further comprising:
    (g) an artificial intelligence module coupled to the calculator configured to alter an importance factor associated with the measurements in calculating the health indicator prior to the calculator determining the value for the health indicator.

11. The system of claim 1 wherein the health indicator is or comprises a prediction of body composition of the individual, the prediction including at least one of total body fat, visceral fat, liver fat, muscle, adipose tissue, fat free mass, subcutaneous fat and bone mass.

12. The system of claim 1 wherein the calculator is arranged to calculate total body volume, and wherein the volume of the individual's head is excluded in the calculation of total body volume.

13. A machine readable medium containing instructions which, when read by a machine, causes the machine to perform a method of generating a health indicator for an individual human being, the method comprising the ordered steps of:
   capturing at least two unique digital photographs of the individual using a first computing device comprising a camera, wherein the at least two unique digital photographs include a front-view image and a side-view image;
   sending demographic information of the individual and the at least two unique digital photographs of the individual from the first computational device to a data collector via an internet connection, using a secure file transfer protocol connection, wherein the demographic information includes gender;
   capturing measurements indicative of body shape from the digital photographs using the data collector and constructing a 3D model of the individual using the received measurements extracted from the captured at least two unique digital photographs;
   retrieving information from a body composition database, the body composition database comprising internal body composition data and corresponding body shape and demographic data of other individual human beings, the retrieved information being selected based on identifying a subset of data in the database based on the received demographic information, and matching the measurements captured by the data collector to body shape data in the identified subset of data in the database;
   determining a value for the health indicator by automatically synthesizing the measurements received from the data collector and the retrieved information from the body composition database;
   returning the health indicator value and the 3D model to the first computing device; and
   using a screen of the first computing device; displaying the 3D model and the health indicator value.

14. The machine readable medium of claim 13, wherein the performed method further comprises, as a part of the provision of the health indicator:
   calculating at least two body volumes using the measurements captured by the data collector;
   creating a first ratio using a body volume of a first body part and a body volume of a second body part;
   storing the measurements and the ratios in a first database; and
   calculating the health indicator using a first formula that utilizes the measurements and ratios as well as coefficients.

15. The machine readable medium of claim 14, wherein the performed method further comprises supplementing the stored information in the first database with information on at least one of: the individual's ethnicity, age and health.

16. The machine readable medium of claim 13, wherein the performed method further comprises the step of altering a coefficient using an artificial intelligence module.

* * * * *